US00PP26442P2

(12) United States Plant Patent
Horvath

(10) Patent No.: US PP26,442 P2
(45) Date of Patent: Mar. 1, 2016

(54) ***PENNISETUM ALOPECUROIDES* PLANT NAMED 'GINGER LOVE'**

(50) Latin Name: *Pennisetum alopecuroides*
Varietal Denomination: Ginger Love

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 154 days.

(21) Appl. No.: 13/998,074

(22) Filed: Sep. 30, 2013

(51) Int. Cl.
*A01H 5/02* (2006.01)

(52) U.S. Cl.
USPC ..... Plt./384

(58) Field of Classification Search
USPC ..... Plt./384
See application file for complete search history.

*Primary Examiner* — Anne Grunberg

(57) ABSTRACT

A new, distinct *Pennisetum alopecuroides* plant as shown and described, characterized by thick red inflorescences on 85 cm stems that start in Mid August in northern Illinois.

1 Drawing Sheet

Latin name: *Pennisetum alopecuroides.*
Cultivar name: 'Ginger Love'.

BACKGROUND OF THE INVENTION

The present invention relates to a new form of *Pennisetum alopecuroides* plant named 'Ginger Love'. 'Ginger Love' is a seedling of an unnamed *Pennisetum alopecuroides*, not patented, characterized by thick red inflorescences on 85 cm stems that start in Mid August in northern Illinois. The new plant is the result of a breeding program taking place at a wholesale perennial nursery since 2001. The seedling was grown by the inventor at a wholesale perennial nursery in Hebron, Ill. in 2010 as an open pollinated seedling from a block of open pollinated unnamed selections. The selection of the new plant was due to its thick red inflorescences on 85 cm stems that start in Mid August in northern Illinois. Asexual, vegetative division propagation has been the only means of reproduction. Propagation has taken place at a wholesale perennial nursery Hebron, Ill. since 2011. To date these plants have remained uniform in height. The new *Pennisetum* has shown to be stable and identical in reproduction to the parent after making over 550 vegetative divisions from 2011 to 2013.

SUMMARY OF THE INVENTION

In the following description, color references are made to The Royal Horticultural Society Colour Chart. The new *Pennisetum alopecuroides* plant named 'Ginger Love' has shown the characteristic of thick red inflorescences on 85 cm stems that start in Mid August in northern Illinois.

Plants of the new *Pennisetum* can be compared to plants of *Pennisetum alopecuroides* 'Red Head', not patented. 1. The new *Pennisetum* has a height of 85 cm compared to the height of *Pennisetum alopecuroides* 'Red Head' which bas a height of 120 cm. 2. The new *Pennisetum* has an inflorescence length of 15 cm compared to *Pennisetum alopecuroides* 'Red Head' which has an inflorescence length of 20 cm.

Plants of the new *Pennisetum* can be compared to plants of *Pennisetum alopecuroides* 'Hameln' not patented. 1. The new *Pennisetum* has a height of 85 cm compared to the height of *Pennisetum alopecuroides* 'Hameln' which has a height of 90 cm. 2. The new *Pennisetum* has an inflorescence length of 15 cm compared to *Pennisetum alopecuroides* 'Hameln' which has an inflorescence length of 10 cm. 3. The new *Pennisetum* has a red inflorescence color compared to *Pennisetum alopecuroides* 'Hameln' which has a tan inflorescence color.

Plants of the new *Pennisetum* can be compared to plants of *Pennisetum alopecuroides* 'Mondry', not patented. 1. The new *Pennisetum* has a height of 85 cm compared to the height of *Pennisetum alopecuroides* 'Moudry' which has a height closer to 60 cm. 2. The new *Pennisetum* has an August bloom time compared to *Pennisetum alopecuroides* 'Mondry' which typically blooms in October.

DESCRIPTION OF PHOTOGRAPHS

Figure 1:
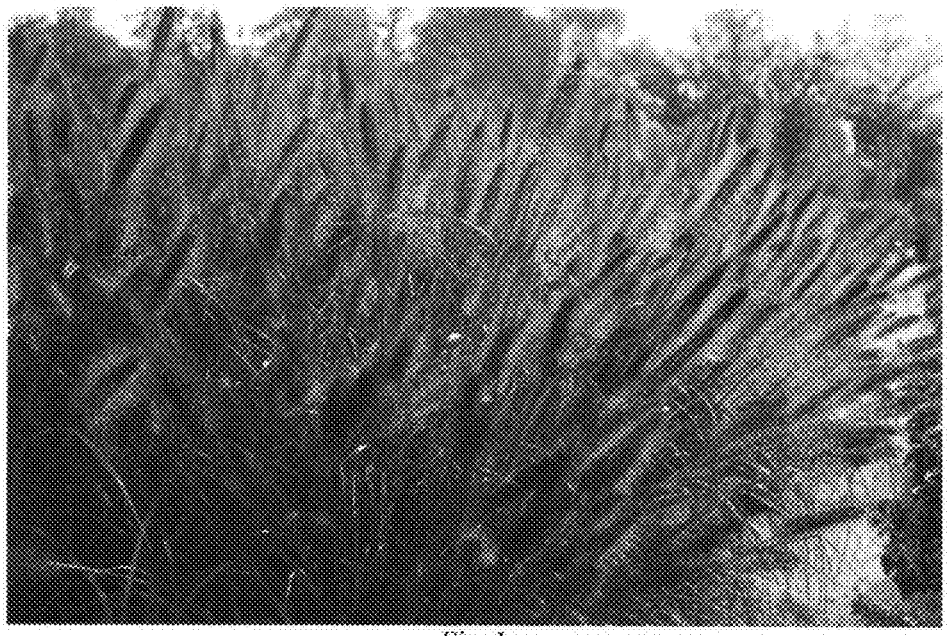
Figure 2:
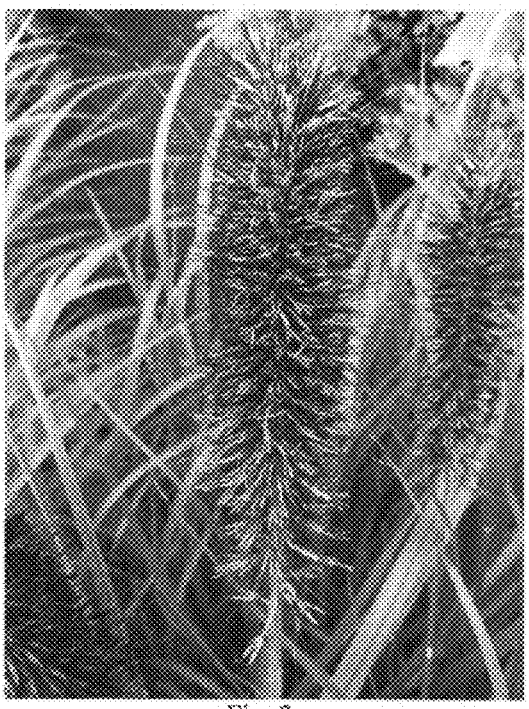

FIG. 1. Shows a group of potted 3 gallon plants.
FIG. 2. Shows a close up of the flower.

DETAILED BOTANICAL DESCRIPTION

In the following description, color references are made to The Royal Horticultural Society Colour Chart. The plant herein described is a one year, three gallon specimen grown in full sun and irrigated in Hebron, Ill.

Botanical classification: *Pennisetum alopecuroides* cultivar 'Ginger love'.

Parentage:
- *Female.*—*Pennisetum alopecuroides* unnamed seedling selection.
- *Male.*—*Pennisetum alopecuroides* unnamed seedling selection.

Propagation: Vegetative division.

Plant description: Overall habit of the new *Pennisetum* is strongly clumping mounds with upright stems topped by red colored flowers in Mid-August. Vigor is moderate to fast.
- *Plant height.*—85 cm.
- *Plant width.*—100 cm.
- *Stem diameter.*—5 mm.

Foliage:
- *Type.*—Deciduous, grass growing in culms.
- *Shape.*—Blade.
- *Petiole.*—None.

*Length.*—59 cm.

*Width.*—9 mm.

*Adaxial leaf description.*—The leaf color is green color 147 B.

*Abaxial leaf description.*—The leaf color is green color 137 C.

Flower inflorescence:

*Inflorescence type.*—Terminal bristled spike.

*Floret color.*—142 C.

*Individual floret size.*—2 mm across, 8 mm tall.

*Bristle size.*—25 mm long, less than 1 mm wide.

*Bristle color.*—N92 A.

*Overall inflorescence spike size.*—6 cm wide, 15 cm long.

*Flower number.*—Approximately 180 florets per mature spike measuring 6 cm wide, 15 cm long.

*Fertility.*—Fertile with 3 Anthers and 3 Stamens.

*Blooming habit.*—Terminal bristled spike on up to 85 cm stems.

*Bloom period and duration.*—Mid-August into October.

*Scent.*—No scent noticed.

*Bloom color overall.*—N 92 A.

*Roots.*—Stiff, fibrous, and freely branching.

*Fruit.*—Seed identical to the species except size is a slightly smaller. Seed color without bristles: ranges from 199 A-199 C. Seed color with bristles: N 77 A.

Disease resistance: Plants are not susceptible to any major pests or diseases.

I claim:

1. A new, distinct *Pennisetum alopecuroides* plant as illustrated and described, characterized by thick red inflorescences on 85 cm stems that start in Mid August in northern Illinois.

* * * * *